United States Patent [19]

Oda et al.

[11] Patent Number: 4,889,551

[45] Date of Patent: Dec. 26, 1989

[54] ISOXAZOLINE DERIVATIVES AND PLANT GROWTH REGULATORS

[75] Inventors: Kengo Oda, Hiratsuka; Tsutomu Ishii, Yokohama; Yukiharu Fukushi, Yokohama; Yuji Enomoto, Yokohama; Makoto Nishida, Yokohama; Yoshikata Hojo, Yokohama, all of Japan

[73] Assignee: Mitsui Toatsu Chemicals, Incorporated, Tokyo, Japan

[21] Appl. No.: 92,197

[22] Filed: Sep. 2, 1987

[30] Foreign Application Priority Data

Oct. 29, 1985 [JP] Japan .................. 60-240666

[51] Int. Cl.$^4$ .................. C07D 261/04; A01N 43/80
[52] U.S. Cl. .................. 71/88; 548/240
[58] Field of Search .................. 71/88; 548/240, 248

[56] References Cited

U.S. PATENT DOCUMENTS

| 4,197,405 | 4/1980 | Liu et al. ............... 548/247 |
| 4,208,510 | 6/1980 | Howe et al. ............ 548/247 |
| 4,209,629 | 6/1980 | Howe et al. ............ 548/241 |

FOREIGN PATENT DOCUMENTS

| 0013111 | 7/1980 | European Pat. Off. . |
| 2062373 | 7/1971 | Fed. Rep. of Germany ...... 548/248 |
| 103070 | 5/1987 | Japan .................. 548/240 |
| 181653 | 4/1966 | U.S.S.R. .............. 548/243 |

OTHER PUBLICATIONS

Chemical Abstract, vol. 107, No. 96708p for JP 103070 (5/13/87).
Chemical Abstracts, 102, 24514d, (1985).
Coutouli-Argyropoulou, Tetrahedron Letters, vol. 25, No. 19, pp. 2029 to 2030 (1984).
Chemical Abstract, vol. 102, No. 24614d for JP 59/137472 (8/7/84).

Primary Examiner—Mukund J. Shah
Assistant Examiner—F. Bernhardt
Attorney, Agent, or Firm—Fisher, Christen & Sabol

[57] ABSTRACT

Novel 3-substituted phenyl-2-isoxazoline-5-carboxylic acids or esters thereof. These compounds have excellent properties as plant growth regulators.

8 Claims, No Drawings

ISOXAZOLINE DERIVATIVES AND PLANT GROWTH REGULATORS

BACKGROUND OF THE INVENTION (a) Field of the Invention

This invention relates to 3-substituted phenyl-2-isoxazoline-5-carboxylic acid and their esters, and plant growth regulators containing the same, more particularly, growth inhibitors and sterilizing agents and to a method for regulating the plant growth by applying the same.

(b) Description of the Prior Art

The plant growth regulators are organic compounds produced in the plant body and control physiological function such as growth, vegetation, organogenesis and the like by migrating through the plant body. These growth regulators are also chemical substances which may be referred to as plant hormones exhibiting their activity in trace amounts, synthetic materials having activity equivalent to these hormones or antiplant harmones having antagonism to these hormones and materials. The plant growth regulators which are currently in practical use include germinating accelerators, rooting accelerators, fruit thinning agents, fruit-drop regulators, growth inhibitors, self-fertiliging agents and the like. The activity, however, is not sharply differentiated but appeared in combination. The emerging activity remarkably varies according to concentration of treatment, growth stage of the plants, part of the plant treated, and the like. For example, 2,4-D (2,4-dichlorophenoxyacetic acid) which is used as a herbicide is also employed for a germinating and rooting agent in a low concentration, and gibberellin which is a phytohormone to accelerate the plant growth is also used as the self-fertilizing agent.

In this invention, the term "growth inhibitor" refers to an agent which creates a stout plant form with a low height by specifically retarding the intermode growth of stalks without affecting the growth of foliage and roots. Crops having such plant form can maintain stable yield of harvest as a result of less break or fall due to a strong wind such as a typhoon etc. Reaping operation of these crops also becomes easier in harvest time. Besides the nutrients which are to be used for the growth are utilized in the edible parts of the plants and thus increase the amount of harvest. Furthermore, trimming operations of turfs can be reduced in parks and golf courses. These effects lead to a remarkable advantage. At present, CCC (2-chloroethyltrimethylammonium chloride) and B-Nine (N-dimethylaminosuccinamic acid) are used as the growth inhibitors and yet restricted to horticultural plants and wheat. Therefore it has been desired to provide highly active growth inhibitors which can be employed for a wide range of crops.

The sterilizing agents may be used for proliferation inhibition of noxious weeds by retarding seminal formation and yet none of them has been known in practical use.

Japanese Patent Laid-open Publication No. 88591/1980 (see also European Published Patent Application No. 0013111) discloses herbicidal activity or growth retarding effect of spiro derivatives of 3-aryl-2-isoxazoline.

Japanese Patent Laid-open Publication Nos. 88591/1980 and 113772/1980 (see also U.S. Pat. No. 4,197,405) disclose examples for applying the above-described spiro derivatives to the preparation of 2-(3-aryl-5-isoxazolyl)benzoic acid derivatives which are useful as the herbicides. In addition, Japanese Patent Laid-open Publication No. 137472/1984 [see also Chemical Abstracts, 102, 24614d, (1985)] discloses examples of employing 3-trifluoromethyl-2-isoxazoline derivatives as intermediates for the preparation of 3-trifluoromethylisoxazole derivatives which have antibacterial activity. Any of the above-described examples however, are limited to utilization as the intermediates.

A new synthetic method of 2-isoxazoline derivatives has been described in Tetrahedron Letters, 25, 2029–2030 (1984) and related compounds of this invention such as methyl 2-(4-chlorophenyl)-2-isoxazoline-5-carboxylate have been written in the examples. No description, however, has been found on their properties and no reference has also been made concerning their physiological effect.

SUMMARY OF THE INVENTION

An object of this invention is to provide a compound having excellent properties as a plant growth regulator, the plant growth regulator containing the same as an effective ingredient, and a method for regulating the plant growth by applying the same.

Precisely, an object of this invention is to provide a compound which is highly active as a plant growth regulator and particularly as a growth inhibitor, can be used for a wider range of crops, not merely inhibits the growth of said crops, but has effect for increasing the yield, and further exerts sterilizing effect by selecting the period and amount of treatment; a pesticide composition containing the same; and a method of regulating the plant growth.

In order to achieve above-mentioned objects, the present inventors have extensively investigated the effect of 2-isoxazoline derivatives on plant physiology. As a result, 3-substituted phenyl-2-isoxazoline-5-carboxylic acid derivatives have been found to be effective for both growth retardation and sterilization of the plants. Thus below described inventions have been achieved.

(1) A 3-substituted phenyl-2-isoxyazoline-5-carboxylic acid and an ester thereof having the formula (I):

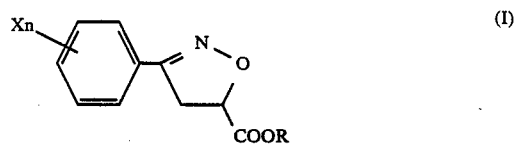

wherein R is a hydrogen atom or a lower alkyl group, X is a halogen atom, lower alkyl group, lower haloalkyl group, lower haloalkoxy group, nitro group, phenoxy group or cyano group, n is 1 or 2, and X may be the same or different when n is 2; where X is a fluorine atom, bromine atom, iodine atom, lower alkyl group having at least 2 carbon atoms, lower haloalkyl group, lower haloalkoxy group, phenoxy group or cyano group when n is 1 and X is at the 4-position.

(2) A plant growth regulator which comprises an effective amount of the compound or the ester thereof having the formula (I), and an agronomically acceptable inert carrier.

(3) A method for the regulation of plant growth which comprises applying to the plant an effectively growth-regulating amount of a 3-substituted phenyl-2- isoxazoline-5-carboxylic acid or an ester thereof having the formula (II):

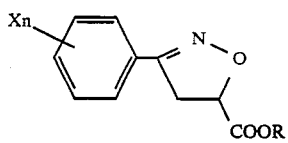

(II)

wherein R is a hydrogen atom or a lower alkyl group, X is a halogen atom, lower alkyl group, lower haloalkyl group, lower haloalkoxy group, nitro group, phenoxy group, or cyano group, n is 1 or 2, and X may be the same or different when n is 2.

DETAILED DESCRIPTION OF THE INVENTION

3-Substituted phenyl-2-isoxazoline-5-carboxylic acid derivatives which are useful as the plant growth regulator of this invention are represented by the aforesaid formula (I). Examples of these derivatives include the following compounds and yet the present invention is not restricted by these compounds.

3-(2-chlorophenyl)-2-isoxazoline-5-carboxylic acid,
3-(3-chlorophenyl)-2-isoxazoline-5-carboxylic acid,
3-(4-chlorophenyl)-2-isoxazoline-5-carboxylic acid,
3-(2-bromophenyl)-2-isoxazoline-5-carboxylic acid,
3-(3-bromophenyl)-2-isoxazoline-5-carboxylic acid,
3-(4-bromophenyl)-2-isoxazoline-5-carboxylic acid,
3-(2-fluorophenyl)-2-isoxazoline-5-carboxylic acid,
3-(3-fluorophenyl)-2-isoxazoline-5-carboxylic acid,
3-(4-fluorophenyl)-2-isoxazoline-5-carboxylic acid,
3-(2-cyanophenyl)-2-isoxazoline-5-carboxylic acid,
3-(3-cyanophenyl)-2-isoxazoline-5-carboxylic acid,
3-(4-cyanophenyl)-2-isoxazoline-5-carboxylic acid,
3-(2-difluoromethoxyphenyl)-2-isoxazoline-5-carboxylic acid,
3-(3-difluoromethoxyphenyl)-2-isoxazoline-5-carboxylic acid,
3-(4-difluoromethoxyphenyl)-2-isoxazoline-5-carboxylic acid,
3-(3-trifluoromethylphenyl)-2-isoxazoline-5-carboxylic acid,
3-(4-trifluoromethylphenyl)-2-isoxazoline-5-carboxylic acid,
3-(2-nitrophenyl)-2-isoxazoline-5-carboxylic acid,
3-(3-nitrophenyl)-2-isoxazoline-5-carboxylic acid,
3-(4-nitrophenyl)-2-isoxazoline-5-carboxylic acid,
3-(3-phenoxyphenyl)-2-isoxazoline-5-carboxylic acid,
3-(4-phenoxyphenyl)-2-isoxazoline-5-carboxylic acid,
3-(5-chloro-2-nitrophenyl)-2-isoxazoline-5-carboxylic acid,
3-(2-chloro-5-nitrophenyl)-2-isoxazoline-5-carboxylic acid,
3-(2,3-dichlorophenyl)-2-isoxazoline-5-carboxylic acid,
3-(2,4-dichlorophenyl)-2-isoxazoline-5-carboxylic acid,
3-(2,5-dichlorophenyl)-2-isoxazoline-5-carboxylic acid,
3-(2,6-dichlorophenyl)-2-isoxazoline-5-carboxylic acid,
3-(3,4-dichlorophenyl)-2-isoxazoline-5-carboxylic acid,
3-(3,5-dichlorophenyl)-2-isoxazoline-5-carboxylic acid,
3-(3,4-dibromophenyl)-2-isoxazoline-5-carboxylic acid,
3-(2,4-dibromophenyl)-2-isoxazoline-5-carboxylic acid,
3-(3,5-dibromophenyl)-2-isoxazoline-5-carboxylic acid,
3-(3-chloro-4-fluorophenyl)-2-isoxazoline-5-carboxylic acid, and their methyl, ethyl, n-propyl, isopropyl, n-butyl, isobutyl, n-pentyl esters, and the like.

The compounds of this invention can be prepared by reacting suitable nitrile oxide with acrylic acid or its ester. Although the reaction rate may be accelerated by warming or under pressure, the reaction is readily carried out at a temperature of from 0° C. to the reflux temperature of reaction solvent.

Since nitrile oxide is unstable and apt to undergo self-condensation, it is better to use it without isolation. That is, in accordance with the following reaction mechanism, suitable hydroxamoyl chloride (III) is reacted with acrylic acid or its ester (IV) in a basic condition to form nitrile oxide (V).

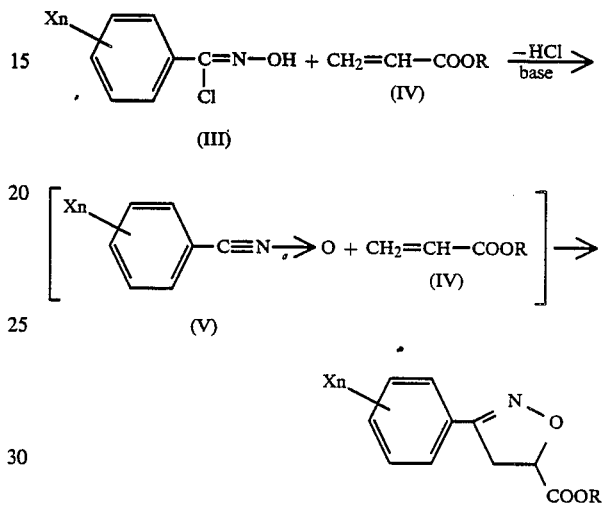

Nitrile oxide (V) thus formed in the reaction mixture is subjected to a ring-forming addition reaction with acrylic acid or its ester (IV) to give the compounds of this invention.

The base used in this invention is an inorganic or organic base having a low nucleophilicity. The examples of the base include as the inorganic base, carbonates such as sodium hydrogen carbonate, potassium carbonate, sodium carbonate, and calcium carbonate, and include as the organic base, tertiary amines such as triethyl amine and pyridine.

The reaction solvent employed is an inert solvent which does not react with the ingredients of this reaction. The solvent includes, for example, ethers such as diethyl ether, tetrahydrofuran and dioxane; ketones such as acetone and methyl ethyl ketone; halogenated hydrocarbons such as dichloromethane, trichloromethane and tetrachloromethane; aromatic hydrocarbons such as benzene and toluene; and aprotic polar solvents such as dimethylformamide, dimethylimidazolidinone and dimethylsulfoxide.

Hydroxamoyl chloride (III) is already known in the art. It is readily prepared according to the following scheme by reacting suitable substituted benzaldehyde (VI) with hydroxylamine and chlorinating the resulting oxime (VII).

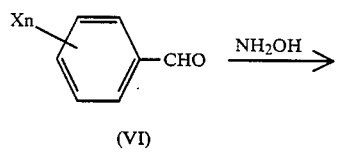

-continued

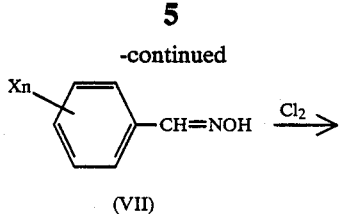

(VII)

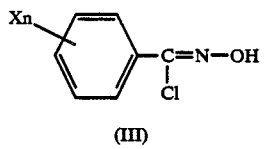

(III)

When R is a hydrogen atom in the afore-mentioned formula (II), the isoxazolinecarboxylic acid of this invention may also be obtained by hydrolyzing isoxazoline-5-carboxylic acid ester of the above formula (II) according to the following scheme.

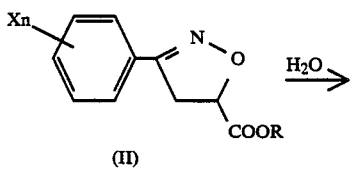

(II)

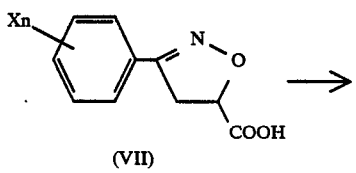

(VII)

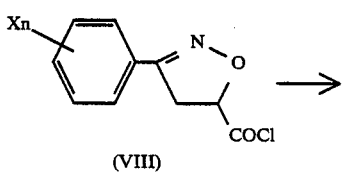

(VIII)

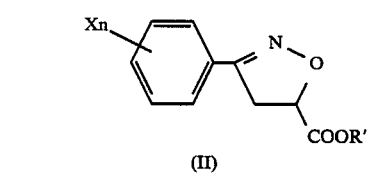

(II)

Furthermore, 3-substituted phenyl-2-isoxazoline-5-carboxylic acid esters may also be prepared by converting thus obtained 3-substituted phenyl-2-isoxazoline-5-carboxylic acid to acid chloride (VIII) and reacting with alcohols in the presence of the base.

When the compounds of this invention are used as a growth inhibitor, the period and amount of treatment differ depending upon the varieties of compounds of this invention, species of crops, types of preparations and various conditions of environment. The treatment period is normally not later than 5-leaf stage, and preferably in the 1- to 3-leaf stage. An applied amount in the range of 1 to 100 g per are of plant growing area is normally suitable and that of 5 to 50 g per are of plant growing area is preferable. The concentration in a sprayable composition is suitably in the range of 100 to 5000 ppm and preferably 500 to 5000 ppm.

The compounds of this invention have an excellent characteristic as the growth inhibitor that causes no die of the crops even by excess use in the above dosages in any growth stage of the crops.

In addition, the compounds of this invention exerts sterilizing effect by selecting the period and amount of treatment. The proliferation of noxious weeds can be inhibited by applying the sterilizing effect and the inhibiting effect toward the weed is further enhanced by the combination of growth retarding effect.

The plant growth regulators of this invention may, of course, be employed in a mixture with other agricultural chemicals such as fungicides, insecticides, herbicides and other plant growth controlling agents; soil conditions; and fertilizers. The compounds of this invention may also be formulated in the preparations together with these agents.

Although the compounds of this invention may be applied as they are, it is preferably applied in the form of a composition in which the active ingredient is mixed with a carrier comprising a solid or liquid diluent. The term "carrier", as used herein, refers to a synthetic or natural inorganic or organic material which aids in the arrival of the active ingredients at a locus to be treated, and facilitates storing, transporting and handling of the active ingredients.

Examples of the suitable solid carriers include clays such as montmorillonite and kaolinite; inorganic materials such as diatomaceous earth, china clay, talc, vermiculite, gypsum, calcium carbonate, silica gel, and ammonium sulfate; plant organic materials such as soybean meal, sawdust, and wheat-flour; and urea.

Examples of suitable liquid carriers include aromatic hydrocarbons such as toluene, xylene, and cumene; paraffinic hydrocarbons such as kerosene and mineral oils; halogenated hydrocarbons such as tetrachloromethane, trichloromethane and dichloroethane; ketones such as acetone and methyl ethyl ketone; ethers such as dioxane and tetrahydrofuran; alcohols such as methanol, propanol and ethylene glycol; dimethylformamide; dimethylsulfoxide and water.

Furthermore in order to enhance the effect of the compounds of this invention, the following adjuvants may also be used either singly or in combination when necessary in consideration of the type of preparations and the field of application.

Examples of the adjuvants which may be employed for emulsification, dispersing, spreading, wetting, binding, stabilization and the like include water soluble bases such as ligninsulfonic acid salts, alkylbenzenesulfonic acid salts, nonionic surface active agents such as alkylsulfuric acid esters, lubricants such as calcium stearate and waxes, stabilizers such as isopropyl hydrogen phosphate, methyl cellulose, carboxymethyl cellulose, casein, and gum arabic. The carriers and adjuvants, however, are not restricted to those materials described above.

The content of active ingredients in the composition of this invention is usually 0.5 to 20% by weight for dusts, 5 to 30% by weight for emulsifiable concentrates, 10 to 90% by weight for wettable powders, and 10 to 90% by weight for flowable preparations.

The properties of the compounds in this invention is illustrated in Table 1. Typical synthesis examples will hereinafter be demonstrated in order to describe the method of preparation in detail, which does not restrict the scope of this invention.

TABLE 1

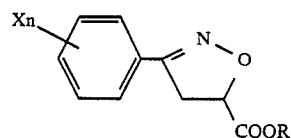
(I)

| Compound No. | Substituent Xn | R | Melting point or Refractive index | Elementary analysis (%) [( ) Calculated value] | | | | | | |
|---|---|---|---|---|---|---|---|---|---|---|
| 1 | 2-Cl | $CH_3$ | $n_D^{20}$ 1.5623 | C; 55.35, (55.13, | H; 4.16, 4.21, | N; 5.59, 5.84, | Cl; 14.91 14.79) | | | |
| 2 | 4-Cl | $CH_3$ | m.p. 70–73 | C; 55.08, (55.13, | H; 3.98, 4.21, | N; 5.91, 5.84, | Cl; 14.83 14.79) | | | |
| 3 | 4-$OCHF_2$ | $CH_3$ | m.p. 44.5–46 | C; 53.23, (53.14, | H; 4.14, 4.09, | N; 5.03, 5.16, | F; 14.23 14.01) | | | |
| 4 | 3-Cl—4-Cl | $CH_3$ | $n_D^{20}$ 1.5881 m.p. 74–75.5° C. | C; 48.38, (48.20, | H; 3.16, 3.31, | N; 5.05, 5.11, | Cl; 25.64 25.87) | | | |
| 5 | 3-$NO_2$ | $CH_3$ | m.p. 99.5–101 | C; 52.94, (52.80, | H; 3.96, 4.03, | N; 11.38 11.20) | | | | |
| 6 | 4-$CH_3$ | $CH_3$ | m.p. 67–68 | C; 66.08, (65.74, | H; 5.76, 5.98, | N; 6.51 6.39) | | | | |
| 7 | 4-Br | $CH_3$ | m.p. 101–103 | C; 46.78, (46.50, | H; 3.68, 3.55, | N; 4.85, 4.93, | Br; 27.84 28.12) | | | |
| 8 | 4-F | $CH_3$ | m.p. 55–59 | C; 59.32, (59.19, | H; 4.36, 4.52, | N; 6.33, 6.28, | F; 8.65 8.51) | | | |
| 9 | 4-CN | $CH_3$ | m.p. 134–135 | C; 62.73, (62.61, | H; 4.27, 4.38, | N; 12.08 12.17) | | | | |
| 10 | 3-Br | $CH_3$ | $n_D^{20}$ 1.5847 | C; 46.65, (46.50, | H; 3.78, 3.55, | N; 4.95, 4.93, | Br; 28.34 28.12) | | | |
| 11 | 2-Cl—4-Cl | $CH_3$ | $n_D^{20}$ 1.5779 | C; 47.83, (48.20, | H; 3.29, 3.31, | N; 5.31, 5.11, | Cl; 26.05 25.87) | | | |
| 12 | 2-Cl—3-Cl | $CH_3$ | $n_D^{20}$ 1.5728 | C; 47.95, (48.20, | H; 3.45, 3.31, | N; 5.22, 5.11, | Cl; 25.67 25.87) | | | |
| 13 | 4-$CF_3$ | $CH_3$ | m.p. 104–105.5 | C; 52.77, (52.76, | H; 3.51, 3.69, | N; 5.08, 5.13, | F; 20.86 21.04) | | | |
| 14 | 3-F | $CH_3$ | $n_D^{20}$ 1.5303 | C; 58.92, (59.19, | H; 4.63, 4.52, | N; 6.21, 6.28, | F; 8.58 8.51) | | | |
| 15 | 3-$OCHF_2$ | $CH_3$ | $n_D^{20}$ 1.5211 | C; 52.97, (53.14, | H; 3.98, 4.09, | N; 5.11, 5.16, | F; 14.20 14.01) | | | |
| 16 | 2-Cl—6-Cl | $CH_3$ | $n_D^{20}$ 1.5527 | C; 47.89, (48.20, | H; 3.55, 3.31, | N; 5.33, 5.11, | Cl; 26.12 25.87) | | | |
| 17 | 4-Cl | $C_2H_5$ | m.p. 51–52 | C; 56.75, (56.82, | H; 4.69, 4.77, | N; 5.59, 5.52, | Cl; 14.04 13.98) | | | |
| 18 | 4-Cl | CH($CH_3$)$_2$ | $n_D^{20}$ 1.5455 | C; 58.24, (58.32, | H; 5.15, 5.27, | N; 5.18, 5.23, | Cl; 13.36 13.24) | | | |
| 19 | 4-Cl | H | m.p. 168.5–169.5 | C; 53.34, (53.23, | H; 3.48; 3.57, | N; 6.33, 6.21, | Cl; 15.65 15.71) | | | |
| 20 | 4-$NO_2$ | $CH_3$ | m.p. 145–147 | C; 53.01, (52.80, | H; 3.98, 4.03, | N; 11.22 11.20) | | | | |
| 21 | 3-Cl—4-F | $CH_3$ | m.p. 76–78 | C; 51.32, (51.28, | H; 3.64, 3.52, | N; 5.51, 5.44, | Cl; 13.78 13.76, | F; 7.33 7.37) | | |
| 22 | 3-$CH_3$ | $CH_3$ | $n_D^{20}$ 1.5493 | C; 65.53, (65.74, | H; 5.63, 5.98, | N; 6.24 6.39) | | | | |
| 23 | 3-O-C$_6$H$_5$ | $CH_3$ | m.p. 94–95 | C; 69.01, (68.68, | H; 5.13, 5.09, | N; 4.64 4.71) | | | | |
| 24 | 2-Cl—5-$NO_2$ | $CH_3$ | m.p. 71.5–73.5 | C; 46.55, (46.41, | H; 3.19, 3.29, | N; 9.81, 9.84, | Cl; 12.70 12.45) | | | |
| 25 | 4-$CF_3$ | H | 151–153 | C; 51.09, (50.97, | H; 2.97, 3.11, | N; 5.32, 5.40, | F; 22.13 21.99) | | | |
| 26 | 3-Cl—4-Cl | H | 150–152 | C; 45.09, (46.18, | H; 2.84, 2.71, | N; 5.22, 5.39, | Cl; 28.01 27.26) | | | |
| 27 | 4-$OCF_3$ | $CH_3$ | 58–59 | C; 48.98, (49.83, | H; 3.25, 3.49, | N; 4.81, 4.84, | F; 19.53 19.71) | | | |
| 28 | 4-$OCF_2Br$ | $CH_3$ | $n_D^{20}$ 1.5222 | C; 41.65, (41.17, | H; 2.64, 2.88, | N; 4.11, 4.00, | Br; 22.01 22.82, | F; 11.21 10.85) | | |

TABLE 1-continued $$\text{(I)}$$

Structure: Xn-phenyl-C(=N-O-)-CH2-CH(COOR) (isoxazoline ring)

| Compound No. | Substituent Xn | R | Melting point or Refractive index | Elementary analysis (%) [( ) Calculated value] |
|---|---|---|---|---|
| 29 | 4-(phenyl-O-) | CH₃ | $n_D^{20}$ 1.5959 | C; 69.23, H; 5.16, N; 4.67 (68.68, 5.09, 4.71) |

SYNTHESIS EXAMPLE 1

Synthesis of 3-(4-chlorophenyl)-2-isoxazoline-5-carboxylic acid methyl ester (Compound No. 2)

4-Chlorophenylhydroxamoyl chloride (1.9 g) and 0.9 g of methyl acrylate were dissolved in 20 ml of tetrahydrofuran. The resulting solution was added dropwise with 1.1 g of triethylamine at 0° to 5° C. over 10 minutes. After reacting for 3 hours at the room temperature, the reaction mixture was poured into water and extracted with toluene. The extracted solution was washed with an aqueous sodium chloride solution, dried over anhydrous sodium sulfate and concentrated under reduced pressure to give 2.2 g (94% yield) of crystalline crude product. The crude product was recrystallized from ethanol to give 1.9 g (82% yield) of desired product having a melting point of 70° to 73° C. The following spectral data were obtained on the recrystallized product.

IR $\nu_{max}^{KBr}$ (cm$^{-1}$); 3070, 2960, 1760, 1600, 1490, 1220, 1030, 900, 830

NMR $\delta_{TMS}^{CDCl_3}$ (ppm); 3.62 (2H, d, J=9 Hz), 3.83 (3H, s), 5.20 (1H, t, J=9 Hz), 7.38 (2H, d, J=9 Hz), 7.62 (2H, d, J=9 Hz)

SYNTHESIS EXAMPLE 2

Synthesis of 3-(4-difluoromethoxyphenyl)-2-isoxazoline-5-carboxylic acid methyl ester (Compound No. 3)

4-difluoromethoxyphenylhydroxamoyl chloride (1.9 g) and 1.0 g of methyl acrylate were dissolved in 20 ml of tetrahydrofuran. The resulting solution was added dropwise with 1.2 g of triethylamine at 0° to 5° C. over 10 minutes. After reacting for 6 hours at the room temperature, the reaction mixture was poured into water and extracted with toluene. The extracted solution was washed with aqueous sodium chloride solution, dried over anhydrous sodium sulfate, concentrated under reduced pressure and purified by silica gel column chromatography (eluent: toluene/ethyl acetate=19/1) to give 1.9 g (74.5% yield) of desired product having a melting point of 44.5° to 46° C. The following spectral data were obtained on the desired product.

IR $\nu_{max}^{KBr}$ (cm$^{-1}$) 3070, 2970, 1750, 1620, 1450, 1250, 1140, 1050

NMR $\delta_{TMS}^{CDCl_3}$ (ppm); 3.58 (2H, d, J=9 Hz), 3.78 (3H, s), 5.16 (1H, t, J=9 Hz), 6.54 (1H, t, J=74 Hz), 7.17 (2H, d, J=9 Hz), 7.70 (2H, d, J=9 Hz)

SYNTHESIS EXAMPLE 3

Synthesis of 3-(4-chlorophenyl)-2-isoxazoline-5-carboxylic acid (Compound No. 19)

3-(4-chlorophenyl)-2-isoxazoline-5-carboxylic acid methyl ester (2.3 g) prepared by the same procedure as in Synthesis Example 1 was dissolved in 20 ml of acetone. The resulting solution was added with 10 ml of water and 0.2 g of p-toluenesulfonic acid, and refluxed by heating for 6 hours. After completing the reaction, the reaction mixture was poured into water. The precipitated crystals were filtered, washed with water, and dried to give 2.1 g of the product as crude crystals. The crude crystals were recrystallized from benzene to give 1.8 g (81% yield) of the desired product having a melting point of 168.5° to 169.5° C. The following spectral data were obtained on the desired product.

IR $\nu_{max}^{KBr}$ (cm$^{-1}$): 3200–2800, 1740, 1605, 1415, 1230, 1110, 900, 830

SYNTHESIS EXAMPLE 4

Synthesis of 3-(4-chlorophenyl)-2-isoxazoline-5-carboxylic acid isopropyl ester (Compound 18)

3-(4-chlorophenyl)-2-isoxazoline-5-carboxylic acid (2.2 g) prepared in Synthesis Example 3 was added with 20 ml of benzene and 1.4 g of thionyl chloride. After refluxing for 30 minutes, the reaction mixture was concentrated under reduced pressure. The resulting residue was dissolved in 20 ml of toluene and added with 0.7 g of isopropyl alcohol. The mixture was further added with 0.8 g of pyridine at 0° to 10° C. and reacted for an hour at the room temperature. The reaction mixture was washed with a dilute aqueous hydrochloric acid solution and successively with water. The resulting solution was concentrated under reduced pressure and then purified by silica gel column chromatography (eluent; toluene) to give 2.0 g (75% yield) of oily desired product.

The following physical property and spectral data were obtained on the product. $n_D^{20}$; 1.5455 IR $\nu_{max}^{neat}$ (cm$^{-1}$); 2980, 1750, 1600, 1500, 1220, 1110, 900, 830

NMR $\delta_{TMS}^{CCl_4}$ (ppm); 1.29 (6H, d, J=7 Hz), 3.48 (1H, d, J=9 Hz), 3.49 (1H, d, J=7 Hz), 4.98 (1H, d, d, J=9 Hz, 7 Hz), 4.98 (1H, m), 7.30 (2H, d, J=9 Hz), 7.54 (2H, d, J=9 Hz)

The following Formulation Examples illustrate the method for preparing the plant growth regulators of this invention.

The active compounds in these examples are designated by Compound numbers given in Table - 1 above. All parts herein mean part by weight.

FORMULATION EXAMPLE 1 (DUST)

Three parts of Compound No. 1, 20 parts of diatomaceous earth, 30 parts of china clay and 47 parts of talc were uniformly pulverized and mixed to give 100 parts of a dust.

FORMULATION EXAMPLE 2 (WETTABLE POWDER)

Twenty parts of Compound No. 2, 57 parts of diatomaceous earth, 20 parts of china clay, 1 part of sodium ligninsulfonate and 2 parts of alkylbenzenesulfonic acid were uniformly pulverized and mixed to give 100 parts of a wettable powder.

FORMULATION EXAMPLE 3 (EMULSIFIABLE CONCENTRATE)

Twenty five parts of Compound No. 3, 65 parts of xylene, and 10 parts of Solpol (surface active agent produced by Toho Chemical Industry Co., Ltd.) were homogeneously mixed to give 100 parts of a emulsificable concentrate.

FORMULATION EXAMPLE 4 (DUST)

Two parts of Compound No. 6, 40 parts of calcium carbonate, and 58 parts of clay were uniformly mixed to give 100 parts of a dust.

FORMULATION EXAMPLE 5 (WETTABLE POWDER)

Fifty parts of Compound No. 5, 40 parts of talc, 5 parts of sodium lauryl phosphate, and 5 parts of sodium alkylnaphthalenesulfonic acid were mixed to give 100 parts of a wettable powder.

FORMULATION EXAMPLE 6 (WETTABLE POWDER)

Fifty parts of Compound No. 6, 10 parts of sodium ligninsulfonate, 5 parts of alkylnaphthalenesulfonic acid, 10 parts of white carbon, and 25 parts of diatomaceous earth were mixed and pulverized to give 100 parts of a wettable powder.

FORMULATION EXAMPLE 7 (FLOWABLE PREPARATION)

Forty parts of Compound No. 7, 3 parts of carboxymethylcellulose, 2 parts of sodium ligninsulfonate, 1 part of sodium dioctylsulfosuccinate and 54 parts of water were wet-pulverized with a sand grinder to give 100 parts of a flowable preparation.

The following Test Examples illustrate the activity of the compounds of this invention as the plant growth regulators.

TEST EXAMPLE 1

Wheat growth retarding test (initial growing period)

Each Wagner pot having a capacity of a/5000 was filled with 3 kg of soil and applied with a compound fertilizer containing each 1 g of N, $P_2O_5$ and $K_2O$ to the entire layer of the soil. A predetermined amount of wheat seeds was sown and covered with the soil. Each pot was placed in a green house under continuous control of water sprinkle to grow the wheat. A wettable powder was prepared from each test compound in accordance with the procedure described in aforesaid Formulation Example 2.

In the 1.5-leaf stage of the wheat, a predetermined amount of the wettable powder diluted with water in an amount corresponding to 10 l per are of plant growing area was sprayed on all over the plants with a micro pressure sprayer. After growing in the green house for 40 days after the application of the chemicals, the growth state of the wheat was examined and the results in Table - 2 were obtained.

TABLE 2

| Compound No. | Amount of compound (g/a) | Herbaceous height (cm) | Ratio to non-treatment (%) |
|---|---|---|---|
| 1 | 25 | 22.7 | 65.2 |
| 2 | 25 | 20.5 | 58.9 |
| 3 | 25 | 21.2 | 60.9 |
| 4 | 25 | 21.5 | 61.8 |
| 5 | 25 | 24.3 | 69.8 |
| 6 | 25 | 23.6 | 67.8 |
| 7 | 25 | 20.8 | 59.8 |
| 8 | 25 | 21.4 | 61.5 |
| 9 | 25 | 24.5 | 70.4 |
| 10 | 25 | 21.3 | 61.2 |
| 11 | 25 | 24.4 | 70.1 |
| 12 | 25 | 22.4 | 64.4 |
| 13 | 25 | 20.5 | 58.9 |
| 14 | 25 | 20.5 | 58.9 |
| 15 | 25 | 21.5 | 61.8 |
| 16 | 25 | 21.0 | 60.3 |
| 17 | 25 | 21.5 | 61.8 |
| 18 | 25 | 22.0 | 63.2 |
| 19 | 25 | 21.7 | 62.4 |
| 20 | 25 | 21.5 | 61.8 |
| 21 | 25 | 24.5 | 70.4 |
| 22 | 25 | 24.5 | 70.4 |
| 23 | 25 | 24.0 | 69.0 |
| 24 | 25 | 23.5 | 66.7 |
| CCC* | 25 | 28.3 | 81.3 |
| B-9** | 25 | 29.2 | 83.9 |
| non-treatment | — | 34.8 | 100.0 |

Note:
*2-chloroethyltrimethylammonium chloride
**N—(dimethylamino)succinamic acid

TEST EXAMPLE 2

Wheat growth retarding test (growing period)

Each Wagner pot having a capacity of a/5000 was filled with 3 kg of soil and applied with a compound fertilizer containing each 1 g of N, $P_2O_5$ and $K_2O$ to the entire layer of the soil. A predetermined amount of wheat seeds was sown and covered with the soil. Each pot was placed in a green house under continuous control of water sprinkle to grow the wheat. An emulsifiable concentrate was prepared from each test compound in accordance with the procedure described in aforesaid Formulation Example 3. In the 2.5-leaf stage of the wheat, a predetermined amount of the emulsifiable concentrate diluted with water in an amount corresponding to 10 l per are of plant growing area was sprayed on all over the plants with a micro pressure sprayer. After growing in the green house until the harvest time, the growth state of the wheat was examined and the results in Table - 3 were obtained. In the examination, herbaceous height, head length and heat weight were measured and indicated as a percentage ratio to those of the wheat grown in the area without treatment.

TABLE 3

| Compound No. | Amount of compound (g/a) | Herbaceous height (% ratio to non-treatment) | Head length (% ratio to non-treatment) | Head weight (% ratio to non-treatment) |
| --- | --- | --- | --- | --- |
| 2 | 5 | 89.8 | 107.1 | 111.3 |
|  | 25 | 90.3 | 109.3 | 121.7 |
| 3 | 5 | 91.9 | 117.1 | 123.4 |
|  | 25 | 71.3 | 117.1 | 118.8 |
| 4 | 5 | 86.4 | 114.0 | 119.3 |
|  | 25 | 80.9 | 108.2 | 126.3 |
| 7 | 5 | 84.7 | 112.5 | 107.5 |
|  | 25 | 89.3 | 118.7 | 113.1 |
| 8 | 5 | 96.8 | 115.6 | 111.4 |
|  | 25 | 91.4 | 110.6 | 115.8 |
| 10 | 5 | 95.1 | 104.6 | 106.7 |
|  | 25 | 87.7 | 108.3 | 112.6 |
| 13 | 5 | 90.7 | 123.4 | 132.6 |
|  | 25 | 79.2 | 114.0 | 121.3 |
| 14 | 5 | 97.1 | 106.4 | 112.4 |
|  | 25 | 91.7 | 104.6 | 114.6 |
| 16 | 5 | 90.7 | 109.3 | 117.4 |
|  | 25 | 89.5 | 120.3 | 130.9 |
| CCC | 5 | 99.0 | 103.1 | 105.7 |
|  | 25 | 98.3 | 109.3 | 110.4 |

The results given in Table - 2 and Table - 3 clearly show that the compounds of this invention have a stronger plant growth inhibiting effect than those of reference compounds from the initiation stage to the growing period. Furthermore, the inhibiting effect accompanies increase in harvest rather than giving no influence on the grain yield.

TEST EXAMPLE 3

Kidney beans growth retarding test

Kidney beans were sown, germimated and grown by the same procedure as in Test Example 2. An emulsifiable concentrate was prepared from each test compound in accordance with the procedure described in aforesaid Formulation Example 3. In the 0.3- to 0.5-leaf stage (6.3 m herbaceous height) of the kidney beams, a predetermined amount of the emulsifiable concentrate diluted with water in an amount corresponding to 10 l per are of plant growing area was sprayed on all over the plants with a micro pressure sprayer. The method beams were grown in the green house. On the 30th days after the application of the chemicals, the herbaceous height was measured and the results in Table-4 were obtained.

TABLE 4

| Compound No. | Amount of compound (g/a) | Herbaceous height cm | (% ratio to non-treatment) |
| --- | --- | --- | --- |
| 2 | 5 | 17.5 | 91.6 |
|  | 25 | 13.6 | 71.2 |
| 4 | 5 | 17.0 | 89.0 |
|  | 25 | 14.0 | 73.3 |

TABLE 4-continued

| Compound No. | Amount of compound (g/a) | Herbaceous height cm | (% ratio to non-treatment) |
| --- | --- | --- | --- |
| 7 | 5 | 16.5 | 86.3 |
|  | 25 | 13.8 | 72.2 |
| 10 | 5 | 17.5 | 91.6 |
|  | 25 | 16.5 | 86.3 |
| 13 | 5 | 16.0 | 83.7 |
|  | 25 | 13.0 | 68.0 |
| CCC | 5 | 18.8 | 98.4 |
|  | 25 | 18.0 | 94.2 |
| non-treatment | 0 | 19.1 | 100.0 |

The results given in Table - 4 show that the compounds of this invention have an appropriate activity as the growth inhibitor also to leguminous plants such as kidney beans.

TEST EXAMPLE 4

Sterilization test

Wheat seeds were sown, germinated and grown by the same procedure as in Test Example 2. An emulsifiable concentrate was prepared from each test compound in accordance with the procedure described in aforesaid Formulation Example 3.

In the 4-leaf stage of the wheat, a predetermined amount of the emulsifiable concentrate diluted with water in an amount corresponding to 10 l per are of plant growing area was sprayed on all over the plants with a micro pressure sprayer. The treated wheats were further grown in the green house until the harvest time. The herbaceous height, head length, head weight, and seed generation in the head (sterilizing rate) were measured and indicated as a percentage ratio to those of the wheat grown in the area without treatment. The results illustrated in Table - 5 were obtained.

TABLE 5

| Compound No. | Amount of compound (g/a) | Herbaceous height (% ratio to non-treatment) | Head length (% ratio to non-treatment) | Head weight (% ratio to non-treatment) | Sterilizing ratio (% ratio to non-treatment) |
| --- | --- | --- | --- | --- | --- |
| 2 | 50 | 84.5 | 109.3 | 73.1 | 100 |
| 3 | 50 | 74.3 | 118.7 | 79.9 | 100 |
| 13 | 50 | 65.2 | 112.5 | 49.1 | 100 |
| CCC | 50 | 90.3 | 93.8 | 90.5 | 0 |
| non-treatment |  | 100 | 100 | 100 | 0 |

As clearly shown in the above descriptions, 3-substituted phenyl-2-isoxazoline-5-carboxylic acid derivatives of this invention have a higher activity as the plant growth inhibitor as compared with conventional agents. The derivatives can be applied to a wide range of crop species and have a broad range of suitable period for application. Furthermore, the derivatives exert the activity for sterilization by selecting the period and amount of treatment. Many applications can be expected in a variety of fields by utilizing these activities.

That is, agricultural chemicals containing 3-substituted phenyl-2-isoxazoline-5-carboxylic acid derivatives are excellent in properties and useful as the plant growth regulators, in particular, as the growth inhibitors and sterilizing agents.

What is claimed is:

1. A 3-substituted phenyl-2-isoxazoline-5-carboxylic acid or an ester thereof having formula (I):

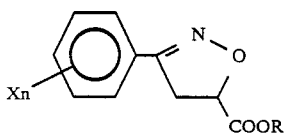 (I)

wherein n is 1 and X is a lower haloalkoxy group or n is 2 and X is the same or different halogen atoms, one of which is at the 4-position, and R is a hydrogen atom or a lower alkyl group.

2. The 3-substituted phenyl-2-isoxazoline-5-carboxylic acid or an ester as claimed in claim 1 wherein, the formula (I), n is 1 and X is a lower haloalkoxy group.

3. The 3-substituted phenyl-2-isoxazoline-5-carboxylic acid or an ester as claimed in claim 1 wherein, in the formula (I), n is 1 and X is the same or different halogen atoms, one of which is at the 4-position.

4. The 3-substituted phenyl-2-isoxazoline-5-carboxylic acid or an ester as claimed in claim 1 wherein, in the formula (I), R is a lower alkyl group.

5. A plant growth regulator composition which comprises a plant growth regulating effective amount of 3-substituted phenyl-2-isoxazoline-5-carboxylic acid or an ester thereof having the formula (I):

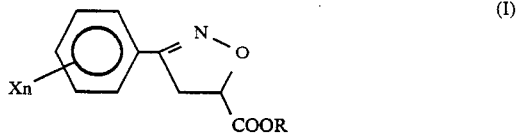 (I)

wherein n is 1 and X is a lower haloalkoxy group or n is 2 and X may be the same or different hlogen atoms, one of hich is at the 4-position, and R is a hydrogen atom or a lower alkyl group; and an agronomically acceptable inert carrier.

6. The plant growth regulator composition as claimed in claim 5, wherein, in formula (I), n is 1 and X is a lower haloalkoxy group.

7. The plant growth regulator composition as claimed in claim 5 wherein, in formula (I), n is 2 and X is the same or different halogen atoms.

8. The plant growth regulator composition as claimed in claim 5 wherein, in formula (I), R is a lower alkyl group.

* * * * *